(12) United States Patent
Hawkes et al.

(10) Patent No.: US 7,445,627 B2
(45) Date of Patent: Nov. 4, 2008

(54) POLYAXIAL PEDICLE SCREW ASSEMBLY

(75) Inventors: David T. Hawkes, Pleasant Grove, UT (US); David R. Warnick, Spanish Fork, UT (US); Michael D. Ensign, Salt Lake City, UT (US)

(73) Assignee: AlpineSpine, LLC, American Fork, UT (US)

( * ) Notice: Subject to any disclaimer, the term of this patent is extended or adjusted under 35 U.S.C. 154(b) by 349 days.

(21) Appl. No.: 11/342,420

(22) Filed: Jan. 30, 2006

(65) Prior Publication Data

US 2006/0173456 A1 Aug. 3, 2006

Related U.S. Application Data

(60) Provisional application No. 60/701,543, filed on Jul. 22, 2005, provisional application No. 60/658,972, filed on Mar. 4, 2005, provisional application No. 60/648,796, filed on Jan. 31, 2005.

(51) Int. Cl.
*A61B 17/58* (2006.01)
*A61F 2/30* (2006.01)

(52) U.S. Cl. ........................ 606/269; 606/266

(58) Field of Classification Search ............ 606/61, 606/250, 251, 269, 264, 265, 266, 267
See application file for complete search history.

(56) References Cited

U.S. PATENT DOCUMENTS

| | | | |
|---|---|---|---|
| 4,950,269 A | 8/1990 | Gaines, Jr. | |
| 5,346,493 A | 9/1994 | Stahurski et al. | |
| 5,443,467 A | 8/1995 | Biedermann et al. | |
| 5,609,593 A | 3/1997 | Errico et al. | |
| 5,647,873 A | 7/1997 | Errico et al. | |
| 5,667,508 A | 9/1997 | Errico et al. | |
| 5,669,911 A | 9/1997 | Errico et al. | |
| 5,683,392 A | 11/1997 | Richelsoph et al. | |
| 5,690,630 A | 11/1997 | Errico et al. | |
| 5,733,285 A | 3/1998 | Errico et al. | |
| 5,817,094 A | 10/1998 | Errico et al. | |
| 5,882,350 A | 3/1999 | Ralph et al. | |
| 5,989,250 A | 11/1999 | Wagner et al. | |
| 6,063,090 A | 5/2000 | Schlapfer | |
| 6,132,432 A | 10/2000 | Richelsoph | |
| 6,248,105 B1 | 6/2001 | Schlapfer et al. | |
| 6,302,888 B1 | 10/2001 | Mellinger et al. | |
| 6,402,752 B2 | 6/2002 | Schaffler-Wachter et al. | |
| 6,485,494 B1 | 11/2002 | Haider | |

(Continued)

*Primary Examiner*—Eduardo C. Robert
*Assistant Examiner*—Ellen Rust
(74) *Attorney, Agent, or Firm*—Bryan G. Pratt; Rader, Fishman & Grauer

(57) ABSTRACT

A fastener and a bone fixation assembly for the internal fixation of vertebral bodies such as a pedicle screw is provided which allows a detachable tulip to be provisionally locked to a pedicle screw, while separately, the rod securely locks to the tulip. According to one exemplary embodiment, the tulip assembly includes a tulip body and an inner tulip member, the tulip body having a non-circular surface disposed on an outer surface. Additionally, a fastener is coupled to the tulip assembly and positionable to retain the tulip assembly on the head of a screw. Further, a cap having an outer surface and a plurality of inner protrusions is provided, wherein the plurality of inner protrusions are configured to mateably connect to the non-circular surface on the tulip body to compress the tulip assembly and secure a rod.

7 Claims, 10 Drawing Sheets

U.S. PATENT DOCUMENTS

| | | |
|---|---|---|
| 6,565,565 B1 | 5/2003 | Yuan et al. |
| 6,641,586 B2 | 11/2003 | Varieur |
| 6,755,829 B1 | 6/2004 | Bono et al. |
| 6,843,791 B2 | 1/2005 | Serhan |
| 6,869,433 B2 | 3/2005 | Glascott |
| 7,087,057 B2 * | 8/2006 | Konieczynski et al. ........ 606/73 |
| 2002/0022842 A1 | 2/2002 | Horvath et al. |
| 2002/0026193 A1 | 2/2002 | Barker et al. |
| 2002/0151900 A1 | 10/2002 | Glascott |
| 2004/0153068 A1 | 8/2004 | Janowski et al. |
| 2004/0158247 A1 | 8/2004 | Sitiso et al. |
| 2004/0172022 A1 | 9/2004 | Landry et al. |
| 2004/0249380 A1 | 12/2004 | Glascott |
| 2005/0033296 A1 | 2/2005 | Bono et al. |
| 2005/0187548 A1 * | 8/2005 | Butler et al. .................. 606/61 |
| 2006/0058788 A1 | 3/2006 | Hammer et al. |

* cited by examiner

POLYAXIAL PEDICLE SCREW ASSEMBLY

RELATED APPLICATIONS

This application claims the benefit under 35 U.S.C. § 119(e) of U.S. Provisional Patent Application No. 60/648,796 filed Jan. 31, 2005; 60/658,972 filed Mar. 4, 2005; and 60/701,543 filed Jul. 22, 2005 each titled "Oval Twist Polyaxial Pedicle Screw Assembly." All of these provisional applications are incorporated herein by reference in their respective entireties.

FIELD

The present system and method relate to bone fixation devices. More particularly, the present system and method provide for a screw assembly configured to facilitate the internal fixation of vertebral bodies.

BACKGROUND

Various devices for internal fixation of bone segments in the human or animal body are known in the art. One type of system is a pedicle screw system, which is sometimes used as an adjunct to spinal fusion surgery, and which provides a means of gripping a spinal segment. A conventional pedicle screw system comprises a pedicle screw, a rod-receiving device, and a rod. The pedicle screw includes an externally threaded stem and a head portion. The rod-receiving device couples to the head portion of the pedicle screw and receives a rod (commonly referred to as a distraction rod). Two such systems are inserted into respective vertebrae and adjusted to distract and/or stabilize a spinal column, for instance during an operation to correct a herniated disk. The pedicle screw does not, by itself, fixate the spinal segment, but instead operates as an anchor point to receive the rod-receiving device, which in turn receives the rod. One goal of such a system is to substantially reduce and/or prevent relative motion between the spinal segments that are being fused.

Although conventional prior art pedicle screw systems exist, they lack features that enhance and/or benefit newer, minimally invasive surgery (MIS) techniques that are more commonly being used for spinal surgeries. It has been suggested that one possible advantage of an MIS approach is that it can decrease a patient's recovery time.

Conventional pedicle screw systems and even more recently designed pedicle screw systems have several drawbacks. Some of these pedicle screw systems are rather large and bulky, which may result in more tissue damage in and around the surgical site when the pedicle screw system is installed during surgery. The prior art pedicle screw systems have a rod-receiving device that is pre-operatively coupled or attached to the pedicle screw. In addition, some of the prior art pedicle screw systems include numerous components that must all be carefully assembled together. Further, traditional pedicle screw systems are pre-operatively assembled, which makes these systems more difficult to install and maneuver in a spinal operation where MIS techniques are used.

SUMMARY

According to one exemplary embodiment, the tulip assembly includes a tulip body, an inner tulip member, and a cap, wherein one or more protruding compression features exist at the interface between the cap and the tulip body to compress the tulip body when the cap is engaged. Additionally, according to one exemplary embodiment, a fastener is coupled to the tulip assembly and positionable to retain the tulip assembly on the head of a screw.

BRIEF DESCRIPTION OF THE DRAWINGS

The accompanying drawings illustrate various exemplary embodiments of the present system and method and are a part of the specification. Together with the following description, the drawings demonstrate and explain the principles of the present system and method. The illustrated embodiments are examples of the present system and method and do not limit the scope thereof.

Figure 1:
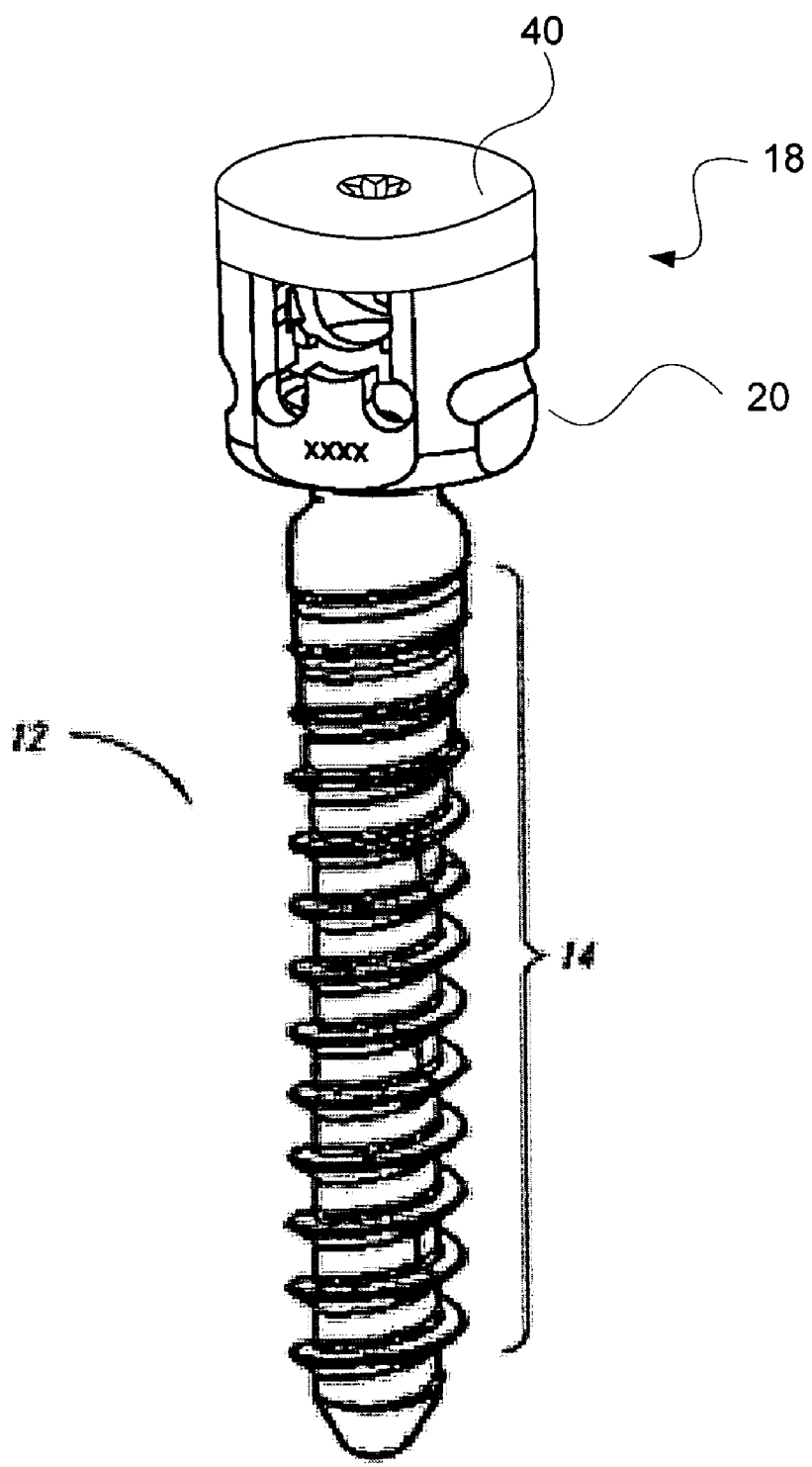
FIG. 1 is an isometric view of a tulip assembly coupled to a pedicle screw according to one exemplary embodiment.

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Throughout the drawings, identical reference numbers designate similar but not necessarily identical elements.

DETAILED DESCRIPTION

The present specification describes a system and a method for separately locking the orientation of a tulip assembly relative to a pedicle screw and locking a positional location of a rod in the tulip assembly. Further, according to one exemplary embodiment, the present specification describes the structure of a tulip assembly configured to be placed on the head of a pedicle screw after placement of the pedicle screw in a patient's body and configured to receive and positionally secure a top loaded rod. Further details of the present exemplary system and method will be provided below.

By way of example, pedicle screw systems may be fixed in the spine in a posterior lumbar fusion process via minimally invasive surgery (MIS) techniques. The systems are inserted into the pedicles of the spine and then interconnected with rods to manipulate (e.g., correct the curvature, compress or expand, and/or structurally reinforce) at least portions of the spine. Using the MIS approach to spinal fixation and/or correction surgery has been shown to decrease a patient's recovery time and reduce the risks of follow-up surgeries.

The ability to efficiently perform spinal fixation and/or correction surgeries using MIS techniques is enhanced by the use of pedicle screw systems provided in accordance with the present exemplary systems and methods, which systems and methods provide a number of advantages over conventional systems. For example, a pedicle screw system in accordance with one embodiment of the present exemplary system and method provides the advantage that the pedicle screw may be inserted into the bone without being pre-operatively coupled with the rod-coupling assembly (hereinafter referred to as a tulip assembly). This is advantageous because the surgeon often needs to do other inter-body work after inserting the pedicle screw, but before attaching the larger and bulkier tulip assembly. Such an advantageous pedicle screw system may be even more crucial when using MIS techniques because the inter-body spatial boundaries in which the surgeon must work may be quite limited.

In addition to accommodating the new MIS approach to lumbar fusion, poly-axial pedicle screw systems in accordance with several embodiments of the present system and method remedy problems common to existing art. First, 'tulip splaying'; which is a post-operative problem of a stressed rod forcing open the tulip and thus disassembling the implanted poly-axial pedicle screw construct is eliminated. Second, pain due to soft-tissue irritation from bulky or high profiled systems is reduced or eliminated.

Further, pedicle screw systems in accordance with several embodiments of the present system and method advantageously allow a user to initially fix (e.g., lock) the tulip assembly to the pedicle screw at a desired angle before fully locking the rod, thereby facilitating compression and distraction of the spinal segments. Initially locking the tulip assembly to the pedicle screw means that at least one of the components of the tulip assembly is manipulated to grip and/or clamp onto the pedicle screw to reduce and/or prevent any translational and/or rotational movement of the tulip assembly relative to the pedicle screw. The ability to initially lock the tulip assembly to the pedicle screw may facilitate the surgeon in performing compression and/or distraction of various spinal and/or bone sections.

The term "distraction," when used herein and when used in a medical sense, generally relates to joint surfaces and suggests that the joint surfaces move perpendicular to one another. However when "traction" and/or "distraction" is performed, for example on spinal sections, the spinal sections may move relative to one another through a combination of distraction and gliding, and/or other degrees of freedom.

Additionally, as used herein, and in the appended claims, the term "non-circular" shall be meant to be understood as any surface profile that has a varying radius when measured from a single point. Consequently, any oval, helical cam, ellipsoid, or other non-circular graduated surface shall be considered, for purposes of the present application, as a non-circular surface.

Another advantageous feature of at least one embodiment of the present exemplary system and method is that an all-inclusive tulip assembly that can be coupled to the head portion of the pedicle screw intra-operatively is disclosed. This advantageous tulip assembly may include the aspects or features that enable the tulip assembly to be initially locked onto the head portion of the pedicle screw and then to further finally lock the rod into the tulip assembly. In one exemplary embodiment, the tulip assembly is initially locked onto the head portion of the pedicle screw after the rod has been received in the tulip assembly. This advantageous tulip assembly may decrease the complexity of the pedicle screw system installation by reducing the installation to essentially a seven-step process including, inserting the pedicle screw into bone, initially snapping the tulip assembly onto the pedicle screw, inserting the rod into the tulip assembly, placing the cap on the tulip assembly to capture the rod in the tulip assembly, rotating the cap to a first position to positionally lock the tulip assembly to the head of the pedicle screw, compressing and/or distracting spinal segments, and then rotating the cap to a second position to finally lock the rod to the tulip assembly. In addition to accommodating the new MIS approach to spinal correction and/or fusion, the present exemplary system and method are configured to eliminate instances of cross-threading and/or post-operative tulip splaying, which occurs when the amount of stress/strain in rod, which may be caused by post-operative back flexion forces open the tulip assembly and eventually leads to the disassembly and/or the failure of the pedicle screw system.

In the following description, certain specific details are set forth in order to provide a thorough understanding of various embodiments of the present polyaxial pedicle screw system. However, one skilled in the relevant art will recognize that the present exemplary system and method may be practiced without one or more of these specific details, or with other methods, components, materials, etc. In other instances, well-known structures associated with pedicle screws have not been shown or described in detail to avoid unnecessarily obscuring descriptions of the embodiments of the invention.

Unless the context requires otherwise, throughout the specification and claims which follow, the word "comprise" and variations thereof, such as, "comprises" and "comprising" are to be construed in an open, inclusive sense, that is as "including, but not limited to."

Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular features, structures, or characteristics may be combined in any suitable manner in one or more embodiments.

Exemplary Structure

Figure 2:
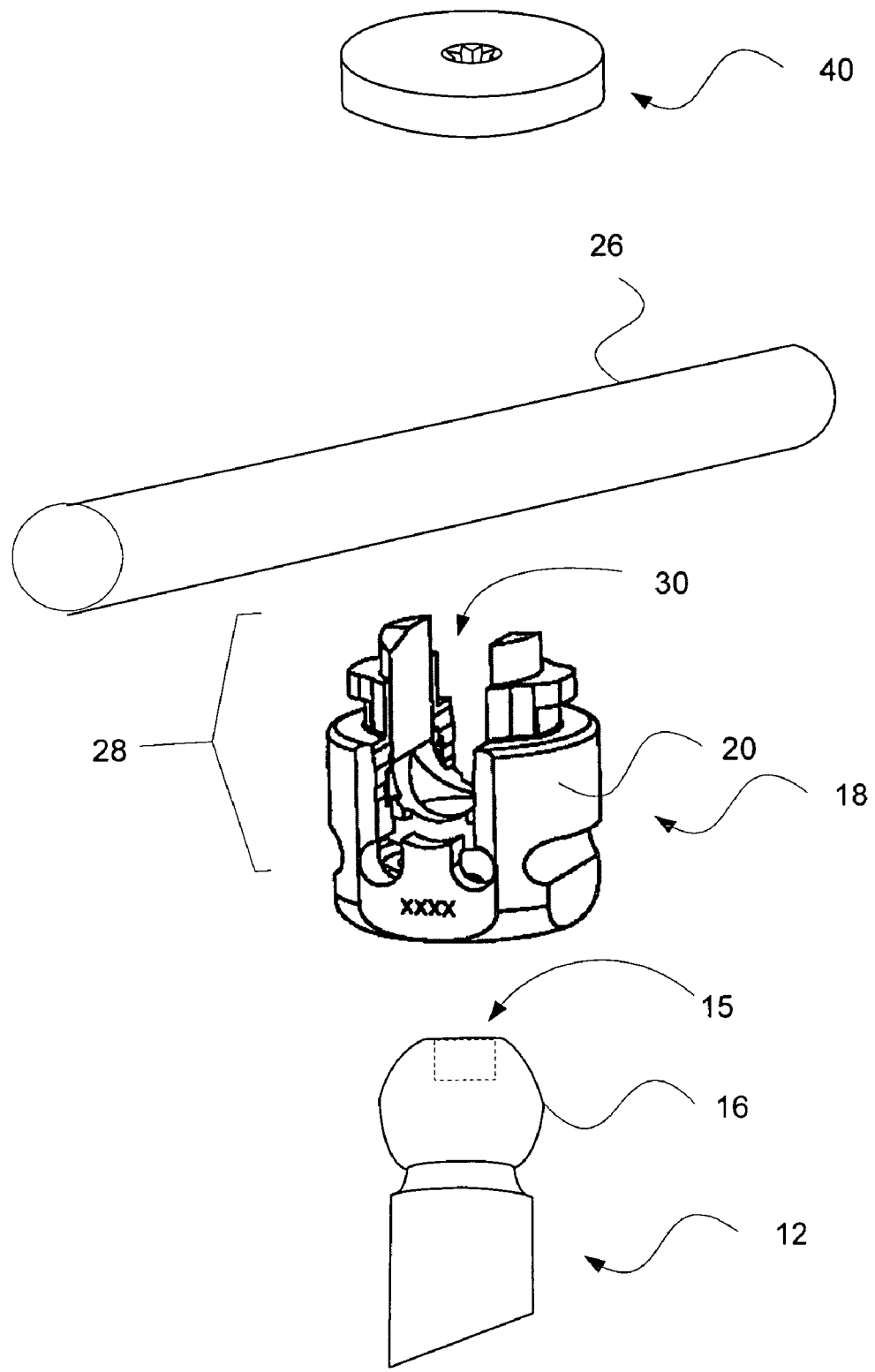
FIG. 2 is an exploded view showing the cap, the tulip assembly, a rod, and the screw of the exemplary embodiment illustrated in FIG. 1.

FIGS. 1 and 2 show the present pedicle screw and tulip assembly (10) according to various exemplary embodiments. As illustrated in FIGS. 1 and 2, the pedicle screw and tulip assembly (10) includes a pedicle screw (12) having a threaded portion (14), a head portion (16) and an interface (15) for driving the screw. The threaded portion (14) is configured to be affixed to the bone of a patient during spine surgery. Additionally, as illustrated in FIGS. 1 and 2, the present exemplary screw and tulip assembly includes a tulip assembly (18) having a tulip body (20), an expansion/contraction member or fastener (22; FIG. 4B), and an inner tulip member (24). As illustrated in FIG. 2, a rod (26) is positioned to be placed in the inner tulip member (24) of the tulip assembly (18) during use. Specifically, the exemplary tulip body (20) illustrated in FIG. 2 has an upper region (28), which includes a rod receiving channel (30) in which the rod (26) is positioned in the final assembly. Further, as shown in FIGS. 1 and 2, the present exemplary pedicle screw and tulip assembly (10) incorporate a cap (40) configured to aid in the coupling of the rod (40) to the tulip assembly (18), and to aid in coupling the tulip assembly to the pedicle screw (12). Further details of the exemplary structural configuration of each component of the present exemplary pedicle screw and tulip assembly (10) will be provided below with reference to FIGS. 3 through 6.

Figure 3:
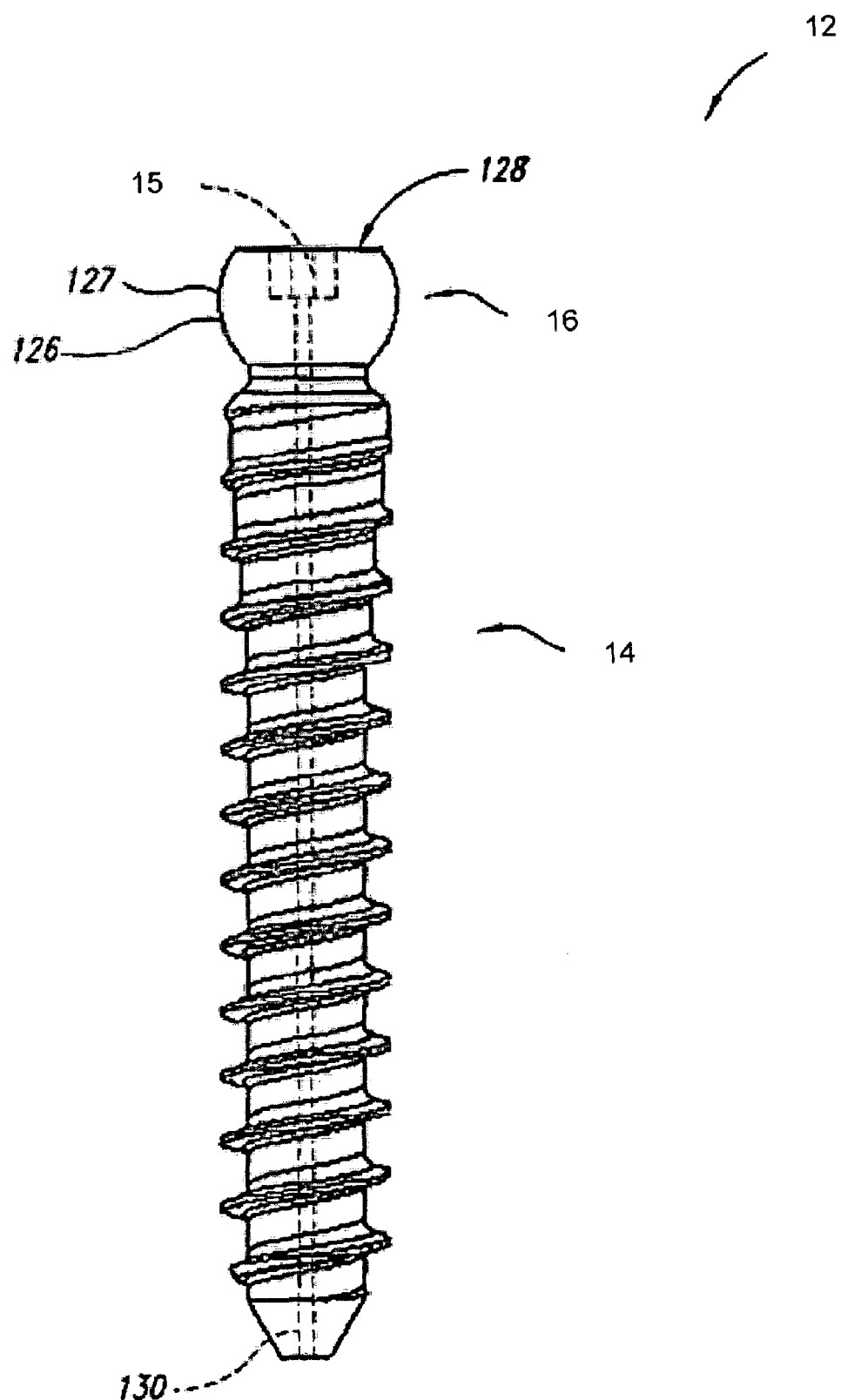
FIG. 3 is a side view of a pedicle screw, according to one exemplary embodiment.

FIG. 3 is a side view of an exemplary pedicle screw, according to one exemplary embodiment. As illustrated in FIG. 3, the pedicle screw (12) includes an elongated, threaded portion (14) and a head portion (16). Although pedicle screws (12) are generally known in the art, the head portions (16) may be of varying configurations depending on what type of tulip assembly (18) is to be coupled to the pedicle screw (12). The head portion (16) of the present exemplary pedicle screw (12) includes a driving feature (15) and a maximum diameter portion (126). The driving feature (15) of the present exemplary pedicle screw (12) permits the screw to be inserted into a pedicle bone and/or other bone. According to one exemplary embodiment, the pedicle bone is a part of a vertebra that connects the lamina with a vertebral body. Additionally, according to the present exemplary embodiment, the driving feature (15) can be used to adjust the pedicle screw (12) prior to or after the tulip assembly (18; FIG. 1) is coupled to the pedicle screw (12). In the illustrated embodiment, the head portion (16) of the pedicle screw (12) is coupled to the threaded portion (14) and includes a generally spherical surface (127) with a truncated or flat top surface (128).

In one exemplary embodiment, the pedicle screw (12) is cannulated, which means a channel (130) (shown in dashed lines and extending axially through the pedicle screw (12)) extends through the entire length of the pedicle screw (12). The channel (130) allows the pedicle screw (12) to be maneuvered over and receive a Kirschner wire, commonly referred to as a K-wire. The K-wire is typically pre-positioned using imaging techniques, for example, fluoroscopy imaging, and then used to provide precise placement of the pedicle screw (12). While the pedicle screw (12) illustrated in FIG. 3 includes a number of components, numerous variations may be made including, but in no way limited to, varying the type of driving feature (15), varying the head shape, varying materials, varying dimensions, and the like.

Figure 4A:
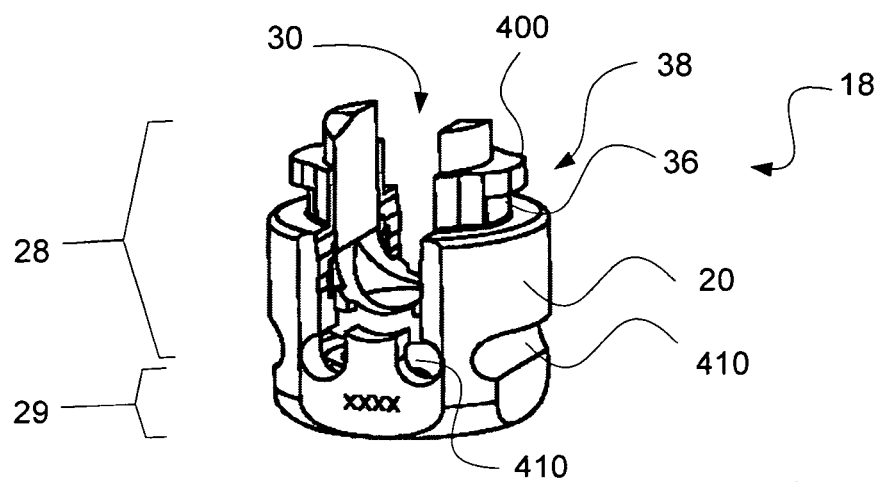
FIG. 4A is a perspective view of an assembled tulip assembly, according to one exemplary embodiment.
Figure 4B:
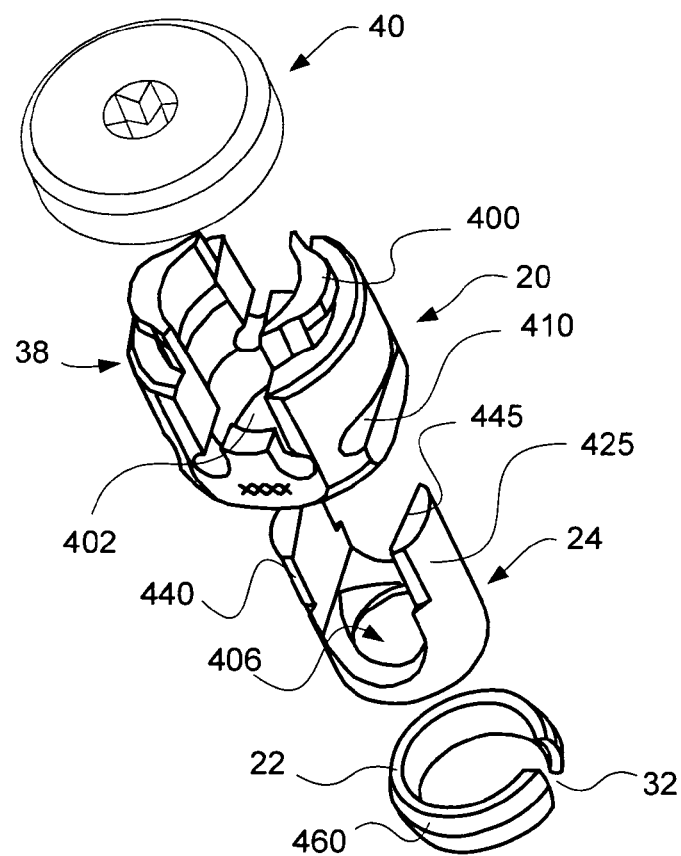
FIG. 4B is an exploded perspective view of the components of the exemplary tulip assembly of FIG. 4A, according to one exemplary embodiment.
Figure 4C:
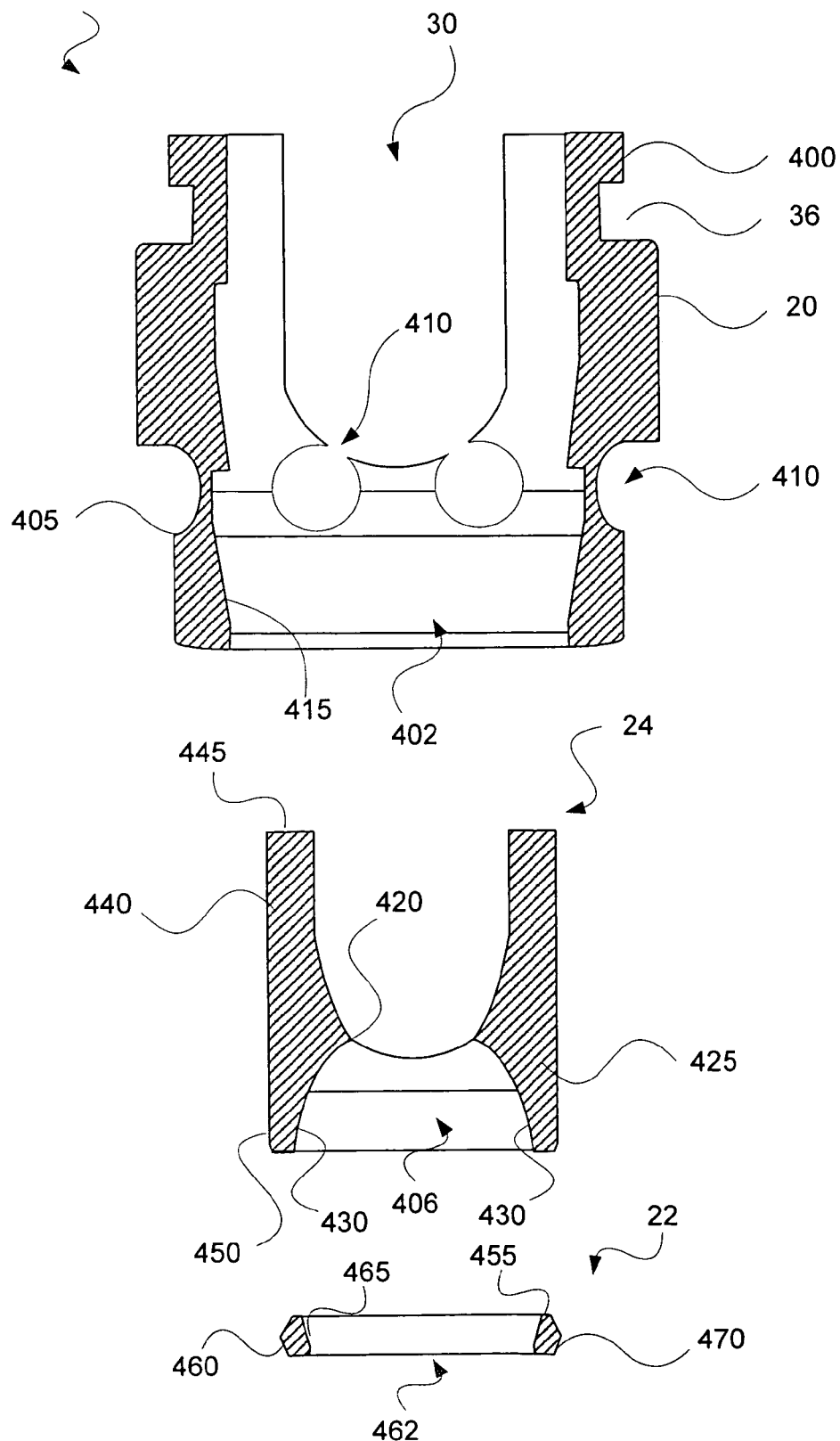
FIG. 4C is an exploded cross-sectional view of the tulip assembly of FIG. 4A, according to one exemplary embodiment.

As mentioned, the pedicle screw and tulip assembly (10; FIG. 1) includes a tulip assembly (18) configured to securely couple both the head (16) of the pedicle screw (12) and a rod (26). FIGS. 4A, 4B, and 4C illustrate a perspective view, an exploded view, and an exploded cross-sectional view, respectively, of an exemplary tulip assembly (18).

As illustrated in the assembled view of FIG. 4A, the exemplary tulip assembly (18) includes an upper portion (28) and a lower portion (29). According to one exemplary embodiment, the upper portion (28) includes a number of features configured to receive and couple a rod (26) thereto. Specifically, as illustrated in FIG. 4A, the upper portion (28) of the tulip assembly (18) includes a rod receiving channel (30) defined by the tulip body (20) and the inner tulip member (24) positioned within the inner bore (402; FIG. 4B) of the tulip body (20). According to one exemplary embodiment, the upper portion of the rod receiving channel (30) is slightly smaller than the diameter of a rod (26; FIG. 2) configured to be retained therein. Further, the rod receiving channel (30) is formed with an increasing tapered width as the rod receiving channel progresses toward the lower portion (29). According to this exemplary embodiment, the initial placement of the rod (26; FIG. 2) in the rod receiving channel (30) will require an initial force to overcome the slight interference fit as the rod progresses down the rod receiving channel. The slight interference fit will provide a temporary lock of the position of the rod (26; FIG. 2), while allowing a surgeon to slideably translate the rod within the tulip assembly (18).

In addition to the rod receiving channel (30), the upper portion (28) of the tulip body (20) can include a number of features that aid in the coupling of the cap (40) and the final locking of the rod (26; FIG. 2). Specifically, as illustrated in the present exemplary embodiment, the upper portion of the tulip body (20) may include a cap retention member (400) and a non-circular compression surface (36). According to one exemplary embodiment, described in further detail below, the cap retention member (400) is configured to interact with components located on the underside of the cap (40) to maintain the cap coupled to the tulip body (20) during installation. As shown, the position of the cap retention member (400) defines a groove (38) configured to receive one or more tabs formed on the cap (40). By incorporating a single groove (38) and a tab coupling system to couple the cap (40) to the tulip body (20), the present exemplary system avoids the issues associated with cross-threading the cap during installation, while providing resistance to splaying of the tulip body. The compression tab (46; FIG. 5B) is disposed in the groove (38) configured to receive the one or more retention tabs.

According to the present exemplary embodiment, any number of non-circular compression surfaces (36) may be formed in the groove (38) to interact with one or more graduated compression tabs (46; FIG. 5B) formed on the underside of the cap (40). According to one exemplary embodiment, the one or more graduated compression tabs (46; FIG. 5B) are configured to be positioned in the groove (38) when the cap (40) is secured on the tulip body (20). According to this exemplary embodiment, described in further detail below, when the cap (40) is rotated, while engaged on the tulip body (20), the graduated compression tabs (46; FIG. 5B) selectively engage the non-circular compression surface (36), creating an interference. Consequently, the upper portion (28) of the tulip body (20) and the inner tulip member (24) are compressed, thereby securing a rod contained within the rod receiving channel (30). While the present exemplary system and method are described in the context of mating compression tabs being present on the cap (40) and a corresponding non-circular compression surface on the tulip body (20), alternative configurations may be used to effect the described compression of the tulip body. Specifically, according to one alternative embodiment, the graduated compression tabs (46) may be present on the cap (40) without mating features existing on the tulip body (20). According to this exemplary embodiment, twisting of the cap (40) can cause the graduated compression tabs (46) to exert a compressive force directly on a circular surface of the groove (38) of the tulip body (20). Conversely, the non-circular compression surface (38) formed in the groove (38) may independently create an interference fit with a cap (40) that has non-graduated compression tabs (46)

Additionally, according to one exemplary embodiment, one or more compression relief(s) (410) may be formed in the tulip body. The compression relief(s) (410) reduces the amount of material that is typically present in the sidewall of the tulip body (20). Consequently, the force required to induce bending in the sidewall of the tulip body (20) during compression of the upper portion (28) of the tulip body (20) is reduced, facilitating a lock of the rod (26; FIG. 2) within the tulip assembly (18). Additionally, according to one exemplary embodiment, selective placement of the compression reliefs (410) may modify the point where bending of the tulip body (20) occurs when the cap (40) is engaged. As illustrated in FIG. 4A, compression relief(s) are formed in the tulip body below the bottom of the rod receiving channel (30). According to this exemplary embodiment, the location of the compression reliefs (410) cause bending to begin at the reliefs, thereby ensuring constriction about a majority of the rod (26).

In addition to the features described above, the present exemplary tulip body (20) also includes a number of features in.the lower portion (29) that facilitate reception of a pedicle screw head portion (16; FIG. 2) and the ability to lock the orientation of the tulip assembly (18) relative to the pedicle screw (12). According to one exemplary embodiment illustrated in FIG. 4C, the tulip body (20) includes a bore (402), a ring expansion channel (405), and a tapered retention bore (415).

According to one exemplary embodiment, the bore (402) is configured to facilitate assembly of the tulip assembly (18) before being placed onto the head portion (16; FIG. 3) of the pedicle screw (12; FIG. 3). In one embodiment, the inner tulip member (24) and the split ring fastener (22) portion of the tulip assembly (18) may be inserted into the tulip body (20) upward through the bore (402) or through the lower portion (29) of the tulip body (20). Additionally, once the tulip assembly (18) is pre-operatively assembled, the bore (402) facilitates reception of the head portion (16; FIG. 3) of the pedicle screw (12; FIG. 3) during the initial coupling of the tulip assembly (18) to the pedicle screw, as will be described in further detail below.

Moreover, as is described below, the tulip body (20) includes a ring expansion channel (405) and a tapered retention bore (415) configured to interact with the split ring fastener (22) during reception and fixation of the head portion (16; FIG. 3) of the pedicle screw (12; FIG. 3). As illustrated in FIG. 4C, the ring expansion channel (405) has a maximum diameter sufficiently large to receive the split ring fastener (22) and accommodate expansion of the split ring fastener as it receives the head portion (16; FIG. 3) of the pedicle screw (12; FIG. 3).

Further, the tapered retention bore (415) is configured to interact with a seating taper (470) of the split ring fastener. According to one exemplary embodiment, the tulip assembly (18) may be positionally fixed relative to the pedicle screw (12), at least partially, by forcing the split ring fastener (22) along the tapered retention bore (415). According to one exemplary embodiment, interaction between the tapered retention bore (415) and the seating taper (470) constricts the split ring fastener (22) about the head portion (16) of the pedicle screw (12), positionally fixing the tulip assembly (18) relative to the pedicle screw.

The exploded views of FIGS. 4B and 4C further illustrate the internal components of the tulip assembly (18) including the inner tulip member (24) and the expansion/contraction member (22), referred to hereafter as the split ring fastener (22).

As shown in FIGS. 4B and 4C, the inner tulip member (24) includes a main body (425) having an inner bore (406) formed therein. The inner bore (406) is substantially concentric with the bore (402) of the tulip body (20) when assembled. Additionally, the inner bore (406) is at least partially defined by a head receiving taper (430) forming an inner surface of the main body (425).

Further, as illustrated in FIG. 4C, the main body (425) includes at least one extension (440) protruding there from, terminating in a top surface (445). The shape of the at least one extension (440) in conjunction with the main body (425) further defines a rod seat (420) configured to receive and interface with the rod (26; FIG. 2). According to one exemplary embodiment, the main body (425) and the extension(s) (440) are sized to be received in the bore (402) of the tulip body (20) and to be rotatable within the tulip body (20). The rod seat (420), along with the inner wall of the extension(s) (440), operates in cooperation with the tulip body (20) to receive, capture, and eventually positionally lock the rod (26; FIG. 2) in the tulip assembly (18). The bottom surface of the inner tulip member (24) forms a split ring interface (450) configured to engage the split ring fastener (22) and force the split ring fastener down in the bore (402) of the tulip body (20), according to one exemplary embodiment. As mentioned, the downward force imparted on the split ring fastener (22) by the split ring interface (450) causes an interaction between the tapered retention bore and the seating taper, resulting in a forced contraction of the split ring fastener (22) on the head portion (16; FIG. 3) of the pedicle screw (12; FIG. 3) sufficient to lock the relative angular position of the tulip body (20) with respect to the pedicle screw (12; FIG. 3).

FIGS. 4B and 4C also illustrate the split ring fastener (22), according to one exemplary embodiment. As shown, the split ring fastener (22) includes a main member body (460) having an expansion gap (32) formed therein. According to one exemplary embodiment, the expansion gap (32) is configured to facilitate the expansion and contraction of the split ring fastener (22) without causing undue stresses on the member material. In addition to the expansion gap (32), the split ring fastener (22) includes a head receiving orifice (462) that is configured to be concentrically aligned with the inner bore (406) of the inner tulip member (24) and the bore (402) of the tulip body (20) when assembled. According to one exemplary embodiment, the head receiving orifice (462) includes a lower head interfacing surface (465) configured to receive the head portion (16; FIG. 3) of the pedicle screw (12; FIG. 3) and further be retained on the head portion of the pedicle screw by the tulip body (20) during a reduction step, as will be described in further detail below.

Additionally, as illustrated in FIGS. 4B and 4C, the split ring fastener (22) includes a seating taper (470) formed in the member body (460). According to one exemplary embodiment, seating taper (470) coincides with the taper retention bore (415) of the tulip body (20). Accordingly, the seating taper (470) is configured to be forced within the taper retention bore (415), by interaction between the split ring interface (450) of the inner tulip member (24) and the engagement surface (455). When the split ring fastener (22) is forced within the tapered retention bore (415), a mechanical advantage is created sufficient to lock the relative angular position of the tulip body (20) with respect to the pedicle screw (12). Particularly, the seating taper (470) of the split ring fastener (22) frictionally contacts the taper retention bore (415) of the tulip body (20), causing a contraction of the split ring fastener (22). In one exemplary embodiment, the split ring fastener (22) is fabricated to be elastically expandable and contractible within the range of operations described herein. While the expansion/contraction member of the present exemplary system is described herein as a split ring fastener (22), tulip assembly (18) can be coupled to the spherical head of the pedicle screw (12; FIG. 3) by any number of fasteners including, but in no way limited to, a collet, a split ring, or other acceptable fastener having features similar to those described above.

Figure 5A:
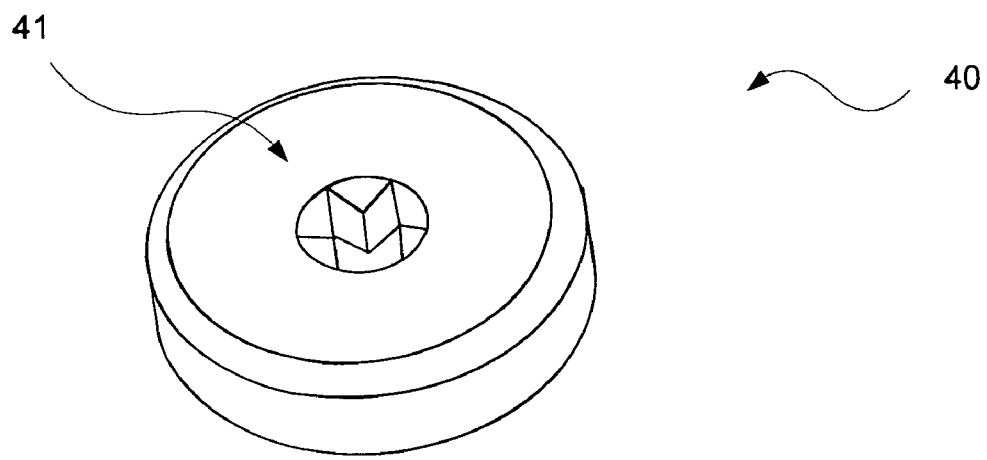
FIGS. 5A and 5B are various perspective views illustrating potential components of the caps, according to one exemplary embodiment.
Figure 5B:
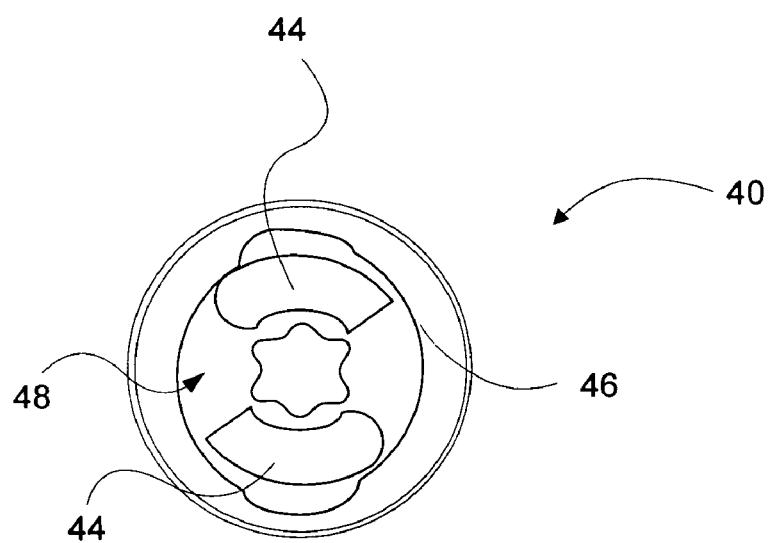

FIGS. 5A and 5B are various views of a cap illustrating both external and internal features of the cap (40) according to one exemplary embodiment. As illustrated in the perspective view of FIG. 5A, the cap (40) may include any number of tool mating features configured to facilitate the imparting of a rotational or other mechanical force on the cap (40) during installation, manipulation, and/or removal. According to the exemplary embodiment illustrated in FIG. 5A, the cap (40) may include a recessed driving feature configured to receive a mating tool.

Turning to FIG. 5B, the underside of the cap (40) includes a number of internal features. According to the exemplary embodiment illustrated in FIG. 5B, the underside of the cap (40) may include, but is in no way limited to, an inner bore (48) that is interrupted by one or more graduated compression tabs (46) and a plurality of inclined planes (44) protruding into the inner bore (48). According to one exemplary embodiment, described in further detail below, the cap (40) is configured to engage the tulip body (20; FIG. 4A) via a number of cut-outs that correspond to the graduated compression tabs (46). When the cap (40) is rotated on the tulip body (20; FIG. 4A), the graduated compression tabs (46) are translated in the groove (38) and retained by the cap retention members (400; FIG. 4A) of the tulip body (20). Further, as described in detail below, rotation of the cap (40) causes the inclined planes (44) and the graduated compression tabs (46) to engage portions of the tulip assembly (18), thereby securely coupling the tulip assembly (18; FIG. 4A) to the pedicle screw (12; FIG. 2), and coupling the rod (26; FIG. 2) to the tulip assembly.

Figure 6:
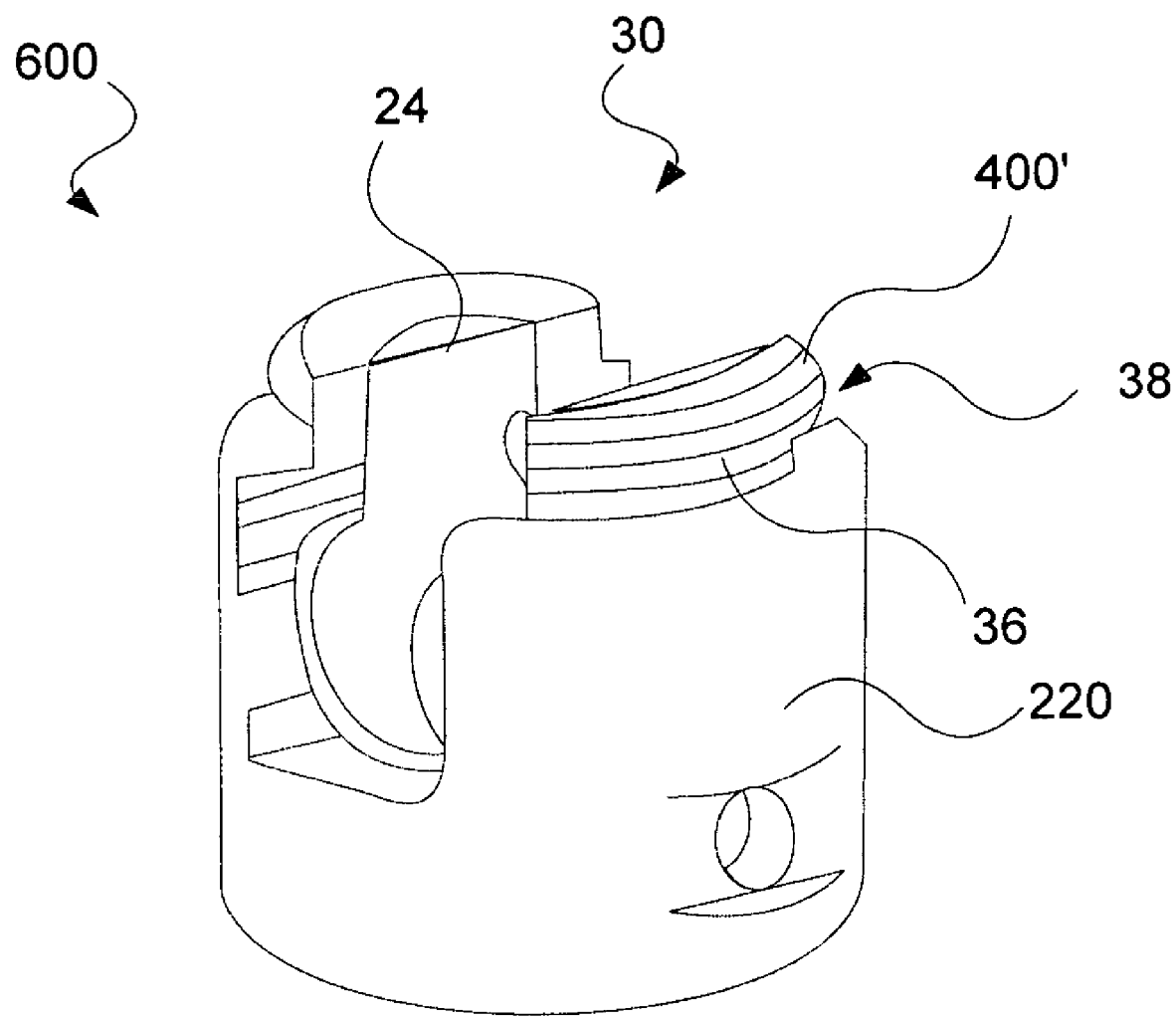
FIG. 6 is a perspective view of an alternative tulip configuration, according to one exemplary embodiment.

While the above-mentioned tulip assembly (18) has been described in detail, any number of modifications in shape and feature combination may be made while still adhering to the teachings of the present exemplary system and method. For example, an alternative tulip housing (600) is illustrated in FIG. 6. As shown, the alternative tulip housing (600) does not include the compression relief (410; FIG. 4A). Rather, the housing of the alternative embodiment illustrated in FIG. 6 has substantially smooth outside walls on the tulip body (20). Further, as illustrated in FIG. 6, the alternative tulip housing (600) has an exaggerated cap retention member (400'). According to the alternative embodiment illustrated in FIG. 6, the exaggerated cap retention member (400') performs the function of both the cap retention member (400; FIG. 4A) and the non-circular compression surface (36) of the exemplary embodiment illustrated in FIG. 4A. Specifically, the exaggerated cap retention member (400') illustrated in FIG. 6 can provide interference induced compression on the alternative tulip housing (600) due to interaction between the graduated compression tabs (46; FIG. 5B) and the exaggerated cap retention members (400'). Further detail of the function and operation of the exemplary tulip assembly (18) will be described below with reference to FIGS. 7-8D.

Exemplary Method

Figure 7:
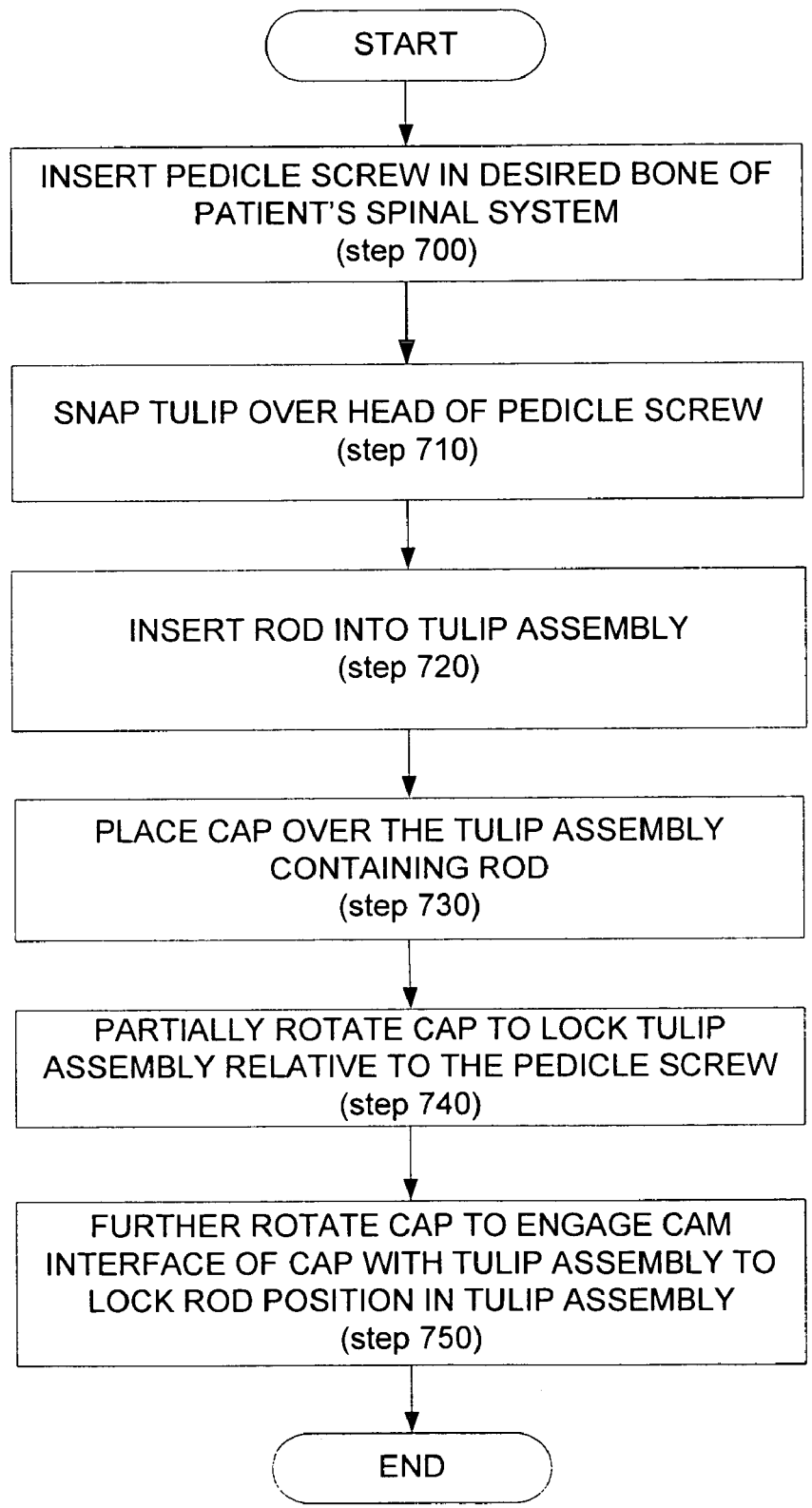
FIG. 7 is a flow chart illustrating a method of securing a tulip assembly and a rod onto a pedicle screw, according to one exemplary embodiment.

FIG. 7 illustrates one method for installing the exemplary pedicle screw and tulip assembly (10; FIG. 1), according to one exemplary embodiment. As illustrated in FIG. 7, the present exemplary method for installing the pedicle screw and tulip assembly (10; FIG. 1) includes inserting one or more pedicle screws in a patient's spinal system (step 700). Once the one or more pedicle screws are inserted in a patient's spinal system, the tulip assembly (18; FIG. 1) is installed over the head of the pedicle screw (step 710). With the tulip assembly snapped over the head of the pedicle screw, the rod may be inserted into the tulip assembly (step 720). The cap may then be placed onto the tulip assembly containing the rod (step 730). After the cap is placed on the tulip assembly, the cap may be partially rotated to lock the position of the tulip relative to the pedicle screw (step 740). The cap may then be fully rotated to engage the graduated compression tabs of the cap with the non-circular compression surface of the tulip assembly to lock the rod position in the tulip assembly (step 750). Further details of each step of the present exemplary method will be provided below with reference to FIGS. 8A through 8D.

As illustrated in FIG. 7, the first step of the exemplary method is to insert one or more pedicle screws in a patient's spinal system (step 700) corresponding to a desired number of pedicle screw and tulip assembly systems (10; FIG. 1). The placement and/or number of pedicle screw and tulip assembly systems (10; FIG. 1) to be used in a patient may be pre-operatively determined based on a pre-operative examination of the patient's spinal system using non-invasive imaging techniques known in the art, such as x-ray imaging, magnetic resonance imaging (MRI), and/or fluoroscopy imaging, for example. Any additional preparation or work is done in order to ensure that the screw (12) is firmly implanted in the proper location in the patient for the particular spine surgery being performed.

Figure 8B:
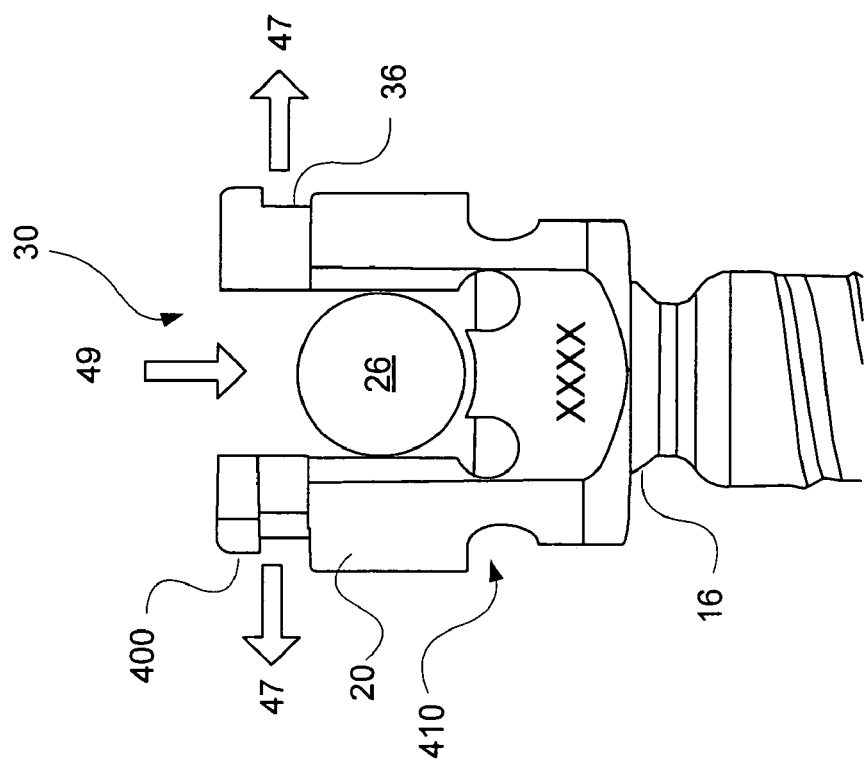
FIG. 8B is an isometric view of the assembly of FIG. 8A further including a rod contained in the saddle, according to one exemplary emboidment.
Figure 8A:
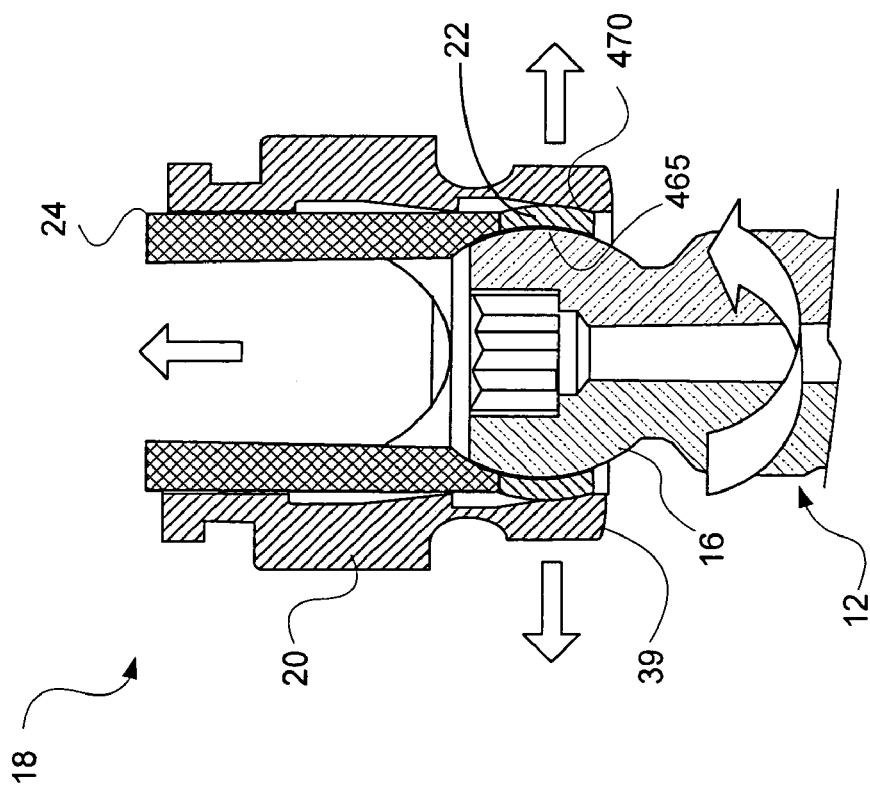
FIG. 8A is an enlarged cross sectional view of the pedicle screw and tulip assembly in a further assembled position, according to one exemplary embodiment.

With the one or more pedicle screws inserted into a patient's spinal system (step 700), the tulip assembly may be snapped over the head of a previously inserted pedicle screw (step 710), as illustrated in FIG. 8A. According to one exemplary embodiment, the tulip assembly (18) may be intra-operatively (i.e., during surgery) coupled to the head portion (16) of the pedicle screw (12) and may be maneuverable to achieve a desired placement, orientation, and/or angular position of the tulip assembly (18) relative to the pedicle screw (12).

According to one exemplary embodiment, when the tulip assembly (18) is snapped onto the head portion (16) of the pedicle screw (12), the lower head interfacing surface (465; FIG. 4C) of the split ring fastener (22) mates with the head portion (16) of the pedicle screw (12). As the tulip assembly (18) is pushed onto the head portion (16) of the pedicle screw (12), the split ring fastener (22) expands and snaps onto the head portion (16). The split ring fastener (22) is initially pushed up into the bore (402; FIG. 4C) of the tulip body (20), as described above. The bore (402; FIG. 4C) in the lower portion (29; FIG. 4A) of the tulip body (20) permits the split ring fastener (22) to float in the bore until it makes contact with ring expansion channel (405; FIG. 4C). Alternatively stated, as the split ring fastener (22) is pushed upwards inside of the tulip body (20) by the head portion (16) of the pedicle screw (12), the split ring fastener (22) expands until sufficient clearance is present for the split ring fastener to expand and snap around the head portion (16) of the screw (12). At this point of the installation method, the tulip assembly (106) may be rotationally coupled to the head portion (16) of the pedicle screw (12). Specifically, as illustrated in FIG. 8A, the compressible ring collapses about the head portion of the pedicle screw in such a way to produce a friction fit; such that the screw maintains poly-axial movement relative to the tulip assembly (18), but requires an appropriate applied force to thus pivot.

As illustrated in FIG. 8A, a reduction step may be performed to somewhat constrict the split ring fastener (22) against the head portion (16) of the pedicle screw (12). With the split ring fastener (22) coupled to the lower half of the head portion (16) of the pedicle screw (12), lifting of the tulip assembly (18) away from the pedicle screw (12) will cause the seating taper (470) of the split ring fastener (22) to engage the tapered retention bore (415) of the tulip body. This engagement will cause the split ring fastener (22) to initially constrict around the head portion (16) of the pedicle screw (12).

During the reduction step, the inner tulip member (24) remains positioned against an inner wall of the tulip body (20). Alternatively, the inner tulip member (24) may also be inserted at this time into the bore (402; FIG. 4C) if the inner tulip member is separate. The inner tulip member (24) may, according to one exemplary embodiment, have a mating outer surface corresponding with the inner surface of the bore (402; FIG. 4C). The split ring fastener (22) is cylindrical, which allows it to move freely within the bore (402; FIG. 4C) in a free state. It may therefore be rotated or tilted at various angles as desired for the particular patient and for proper connecting to the rod to what the desired angle as determined by the physician during the surgical procedure.

Once the tulip assembly (18) is disposed on the pedicle screw (12), the tulip assembly may then be rotated to achieve a desired orientation with respect to the pedicle screw so that the tulip assembly (18) may receive a rod (26; FIG. 2). It is understood that the relative angular position of a first tulip assembly (18) to a first pedicle screw (12) may be different from the relative orientation of other pedicle screw and tulip assembly (10; FIG. 1) located elsewhere on a patient's spine. In general, the relative, angular position of the tulip assembly (18) to the pedicle screw (12) allows the surgeon to selectively and independently orient and manipulate the tulip assemblies (20) of each pedicle screw and tulip assembly (10; FIG. 1) installed into the patient to achieve and/or optimize the goals of the surgical procedure, which may involve compressing, expanding, distracting, rotating, reinforcing, and/or otherwise correcting an alignment of at least a portion of a patient's spine.

Once the tulip assembly (18) is positioned, the rod can be snapped into the rod slot of the tulip (step 720; FIG. 7). As illustrated in FIG. 8B, the rod receiving channel (30) in the tulip body (20) is smaller in width than the rod (26). Consequently, the rod (26) elastically expands the rod receiving channel (30) in the tulip as the rod passes down the rod slot, as illustrated by the arrows (47). According to one exemplary embodiment, the rod receiving channel (30) of the tulip assembly (18) has a concavity machined in the walls at the proper final rod position that captures the rod by allowing recovery of the elastic deformation of the rod receiving channel. The concavity is sized such that the rod (26) is still free to slide along its axis in the tulip assembly (18).

Figure 8D:
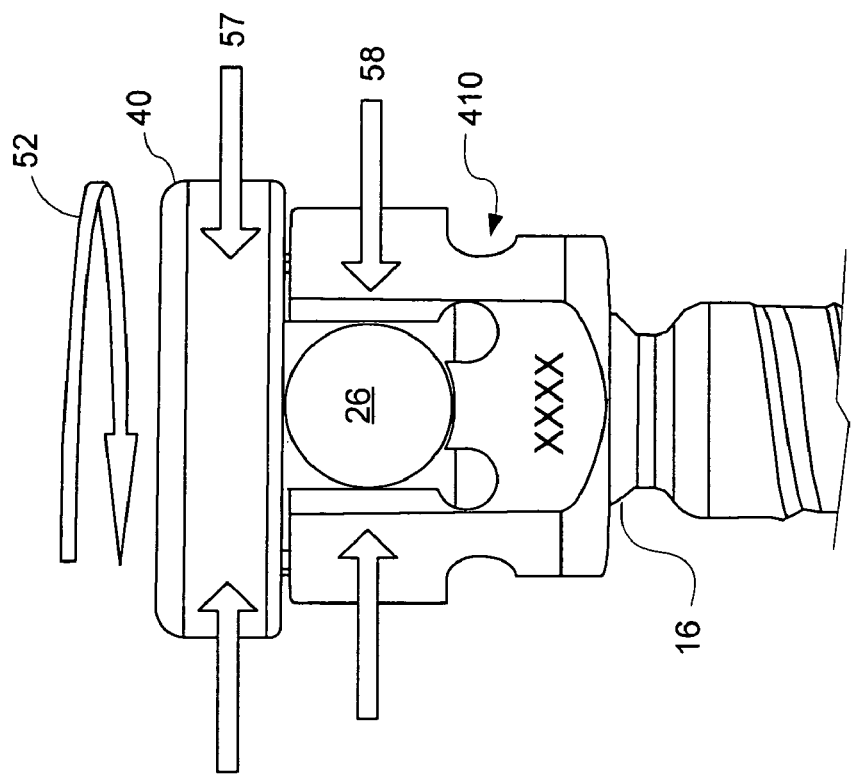
FIG. 8D is an isometric view of the assembly of FIG. 8C, further including the cap in a retained position to lock the rod to the tulip assembly in accordance with one exemplary embodiment.
Figure 8C:
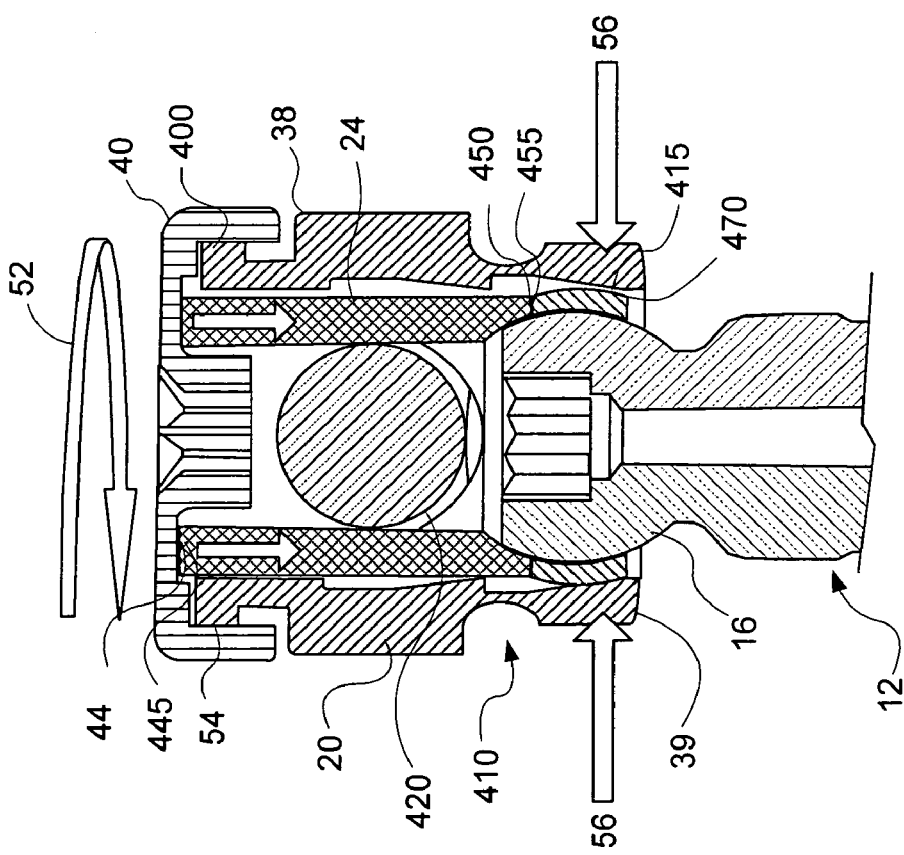
FIG. 8C is an enlarged cross sectional view of the pedicle screw and tulip assembly in a further assembled position with the cap partially rotated to provide a provisional lock of the tulip assembly to the head of the screw in accordance with one exemplary embodiment.

With the rod (26) inserted in the rod receiving channel (30), the cap is placed over the rod and tulip assembly (step 730; FIG. 7). FIG. 8C illustrates the cap (40) engaged with the tulip assembly (18). As illustrated, when the cap (40) engages the tulip assembly, the graduated compression tabs (46; FIG. 5B) are aligned with the upper groove (38; FIG. 4B) of the tulip body. Additionally, as illustrated in FIG. 8C, when the cap (40) is placed over the tulip assembly (18), the inclined planes (44) are positioned adjacent to the top surface (445) of the inner tulip member (24).

After the cap (40) is placed on the tulip assembly (18), the cap can be partially rotated to lock the angular position of the tulip assembly relative to the pedicle screw (step 740; FIG. 7). As illustrated in FIG. 8C, partial rotation of the cap (40) on the tulip assembly (18) causes the inclined planes (44) of the cap to engage the top surface (445) of the inner tulip member (24). As the inclined planes (44) engage the top surface (445) of the inner tulip member (24), they impart a downward force, as illustrated by the downward arrows in FIG. 8C. The downward force imparted on the top surface (445) of the inner tulip member (24) is translated through the inner tulip member and acts upon the split ring fastener (22). As the split ring interface (450) of the inner tulip member (24) contacts the engagement surface (455) of the split ring fastener (22), the split ring fastener is forced further into the tapered retention bore (415) of the tulip body (20). As mentioned previously, forcing the split ring fastener (22) down the tapered retention bore (415) engages the seating taper (470) and the tapered retention bore, which compresses the split ring fastener about the screw head and rigidly locks the tulip assembly (18) to the pedicle screw (12). However, according to one exemplary embodiment, the rod (26) is still free to translate along its axis in the tulip assembly.

Next, the cap is further rotated to engage the graduated compression tabs (46) of the cap (40) with the non-circular compression surface (36) of the tulip body (step 750; FIG. 7). As illustrated in FIG. 8D, when the cap (40) is rotated the graduated compression tabs (46) on the cap (40) slide into the groove (38) of the tulip body (20) to further retain the cap (40) on the tulip assembly (18) and to engage the non-circular compression surface (36).

As shown in FIGS. 7C and 7D, engagement of the non-circular compression surface (36) and the graduated compression tabs (46) causes a compression along the direction of arrows 57, 58, of the rod receiving channel (30; FIG. 4C). As the rod receiving channel is compressed, the rod (26) is rigidly locked to the tulip assembly (18). More particularly, according to one exemplary embodiment, rotation of the cap (40) creates a force that is applied in the direction shown by arrow 54 to push the rod (26) down into the tulip body (20). This is done preferably by rotating the cap (40) as shown by the arrow (52). As the inner tulip member (24) is pressed down into the tulip body (20), a compression force at arrows 58 is applied to the inner tulip member to more solidly press against the rod (26) and greatly increase the gripping force with which the rod is held. The inner surface of the tulip body (20) has a shape configured to apply pressure to the outer portions of the inner tulip member (24). This may be achieved, for example, by having a taper in the inner surface of the tulip body (20) so that pressure is applied against the inner tulip member (24) as it is depressed into the tulip body (20). Alternatively, the inner tulip member (24) may have a slightly increasing taper in its outer diameter so that additional pressure is applied as the inner tulip member is pressed into the straight wall of the inner portion of the tulip body (20). Additional alternative shapes may also be provided by which increased frictional pressure on the rod (26) is provided as the inner tulip member is pressed into the tulip body (20) as shown at arrows 58.

Additionally, as the rod (26) and the inner tulip member (24) are pressed down into the tulip body (20), the extensions (440) are compressed, further increasing the compression on the head portion (16) of the pedicle screw (12). Consequently, completing the rotation of the cap (40) securely locks the rod (26) in the tulip assembly (18), while finally locking the relative position of the tulip assembly relative to the pedicle screw (12).

The preceding description has been presented only to illustrate and describe the present method and system. It is not intended to be exhaustive or to limit the present system and method to any precise form disclosed. Many modifications and variations are possible in light of the above teaching.

The foregoing embodiments were chosen and described in order to illustrate principles of the system and method as well as some practical applications. The preceding description enables others skilled in the art to utilize the method and system in various embodiments and with various modifications as are suited to the particular use contemplated. It is intended that the scope of the present exemplary system and method be defined by the following claims.

What is claimed is:

1. A pedicle screw assembly comprising:
a threaded screw, the screw having a threaded portion, a spherical head and an interface for driving the screw;
a tulip assembly including a tulip body and an inner tulip member slideably disposed within said tulip body, the tulip body having non-circular surface disposed on an outer surface,
a fastener coupled to the tulip assembly and positionable to retain the tulip assembly on the head of the screw, wherein said fastener comprises a compression ring including a split in the ring, wherein said fastener is configured to vary from a first diameter to a second diameter to receive and be positioned around at least a part of the head portion of said threaded screw; and
a cap having an outer surface and a plurality of graduated compression tabs, wherein said plurality of graduated compression tabs are configured to mateably connect to said non-circular surface to compress said tulip assembly;
wherein said cap further comprises a plurality of protruding members on an inner surface of said cap, said protruding members being configured to selectively engage said inner tulip member and impart a translating force on said inner tulip member when said cap is rotated;
wherein said tulip body includes an internal wall region defining a bore, said bore being configured to receive said fastener and said inner tulip member, said bore extending from a top region of the tulip to a lower region of the tulip, said bore being sized to receive said spherical head of said screw, and said bore including an expansion channel shaped to facilitate coupling of said fastener to said spherical head of said screw when inserted in said bore, wherein said expansion channel further comprises a seating taper disposed on a lower portion of said expansion channel, and a taper disposed on a lower portion of said fastener corresponding to said seating taper, wherein said seating taper and said taper on said fastener are configured to engage to constrict said fastener about said spherical head of said screw;
wherein said inner tulip member is coupled in said tulip body adjacent to said fastener such that a downward translation of said inner tulip member translates said fastener into a seating taper;
wherein said protruding members are configured to impart said translating force on said inner tulip member sufficient to seat said fastener in said seating taper to lock an angular position of said tulip assembly relative to said threaded screw; and
wherein said cap has a first position and a second retained position, said first cap position engaging said protruding members and said inner tulip member sufficient to lock a relative angle between said tulip assembly and said threaded screw, and said second retained position engaging said graduated compression tabs with said non-circular surface of said tulip body to compress said tulip assembly sufficient to lock a rod within said tulip assembly.

2. The pedicle screw assembly of claim 1, wherein said protruding members comprise inclined planes.

3. The pedicle screw assembly of claim 1, wherein said tulip body further comprises at least one compression relief.

4. The pedicle screw assembly of claim 1, further comprising a coupling member formed on said tulip body;
wherein said coupling member defines a single channel, said non-circular surface being disposed in said channel; and
wherein said graduated compression tabs in said cap connect to and are rotated in said channel.

5. The pedicle screw assembly of claim 1, wherein said cap further comprises a tool receiving driving feature.

6. A tulip assembly configured to be coupled to a head of a bone fixation device comprising:
an outer member including a non-circular surface;
a first inner member disposed in a lower portion of said outer member and a second inner member disposed in an upper portion of said outer member, said first inner member and said second inner member being configured to fix said tulip assembly to said head of a bone fixation device;
a channel formed in said tulip assembly to receive a rod; and
a cap having an outer surface and a plurality of graduated compression tabs and a plurality of inclined planes, wherein said graduated compression tabs are configured to mateably connect to said non-circular surface to compress said channel
wherein said first inner member is elastically expandable to receive said head of a bone fixation device;
said second inner member including:
a main body;
at least one extension proximally protruding from said main body;
an inner bore formed in a distal end of said main body; and
a compression surface formed on a distal end of said main body;
wherein said compression surface is configured to contact said first inner member and selectively seat said first inner member in a seating taper, said seating taper being configured to constrict said first inner member about said head of a bone fixation device to fix a position of said tulip assembly relative to said bone fixation device; and
wherein said cap has a first position and a second retained position, said first position being configured to engage said plurality of inclined planes with said first inner member to seat said first inner member and to lock a relative angle between said tulip assembly and said threaded screw, and wherein said second retained position engages said graduated compression tabs with said non-circular surface to compress said channel to lock a rod within said tulip assembly.

7. A pedicle screw assembly comprising:
a threaded screw, the screw having a threaded portion, a spherical head and an interface for driving the screw;
a tulip assembly including a tulip body and an inner tulip member, the tulip body including an inner surface and an outer surface, said inner surface defining a bore for receiving said inner tulip member, and a non-circular surface disposed on said outer surface;
a split ring fastener coupled to the tulip assembly and positionable to retain the tulip assembly on the head of the screw; and
a cap having an outer surface and a plurality of graduated compression tabs and a plurality of inclined planes, wherein said cap has a first position and a second retained position, wherein said first position engages said plurality of inclined planes with said inner tulip member to lock a relative angle between said tulip assembly and said threaded screw, and wherein said second retained position engages said graduated compression tabs with said non-circular surface to compress said tulip assembly to lock a rod within said tulip assembly;

wherein said bore extends from a top region of the tulip assembly to a lower region of the tulip assembly;

wherein said bore is sized to receive said spherical head of said threaded screw; and said bore includes an expansion channel shaped to facilitate coupling of said fastener to said spherical head of said screw when inserted in said bore; and wherein said expansion channel further comprises a seating taper disposed on a lower portion of said expansion channel, and a taper disposed on a lower portion of said split ring fastener corresponding to said seating taper, wherein said seating taper and said taper on said fastener are configured to constrict said fastener about said spherical head of said screw.

* * * * *